Dec. 10, 1946. H. C. SWIM Plant Pat. 717
ROSE PLANT
Filed Jan. 17, 1946
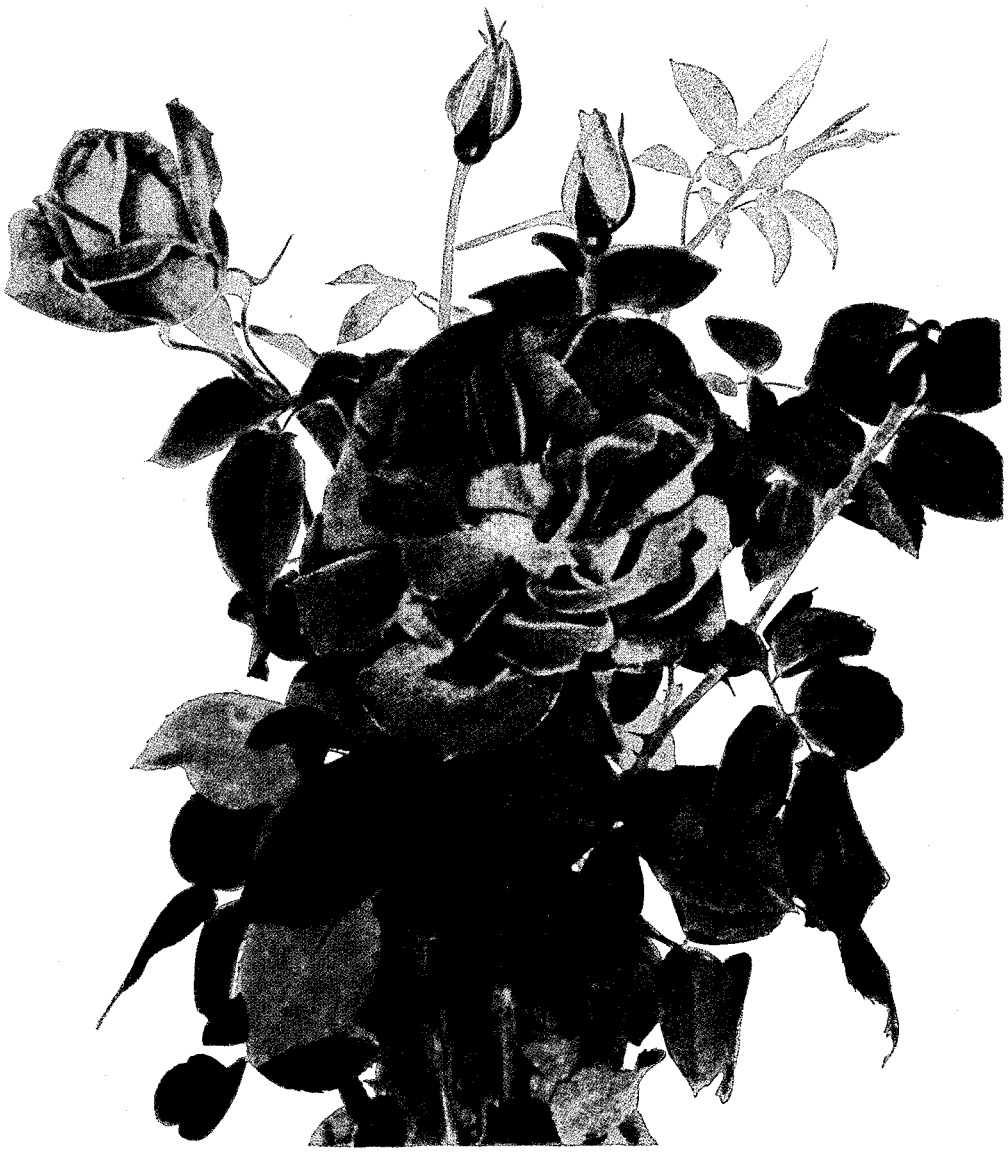
Inventor
H. C. Swim
By Robb & Robb
attorneys Patented Dec. 10, 1946

Plant Pat. 717

UNITED STATES PATENT OFFICE

717

ROSE PLANT

Herbert C. Swim, Ontario, Calif., assignor to Armstrong Nurseries, Inc., Ontario, Calif., a corporation of California Application January 17, 1946, Serial No. 641,682

1 Claim. (Cl. 47—61)

This invention relates to a new and distinct variety of rose plant resulting from a cross of the two known varieties of "Charlotte Armstrong" (Pl. Pat. #455) and "Piccaninny."

The new rose is so completely distinguished from either of its parents that it may well be said that any similarity thereto is quite insignificant. The nearest to a similarity is found in the fragrance of its flowers relative to that of "Piccaninny" in that both are spicy, but "Piccaninny" is possessed of a penetrating fragrance, whereas that of this new variety is only moderate. Outside of this and a slight resemblance in the bark of the canes and amount of thorns, the new rose is definitely distinct from its parents and any other comparable variety of rose.

The primary features of distinction consist in its habit of growth and branching, its vigor, the size, shape, texture, and appearance of the leaves, the shape of its open flowers and their color. More specifically, three-day-open blooms are unique in two respects, i. e., the lateral margins of the petals are reflexed in such a manner as to frequently give to them a slender, linear-oblong appearance in outline. These lateral margins also prop each succeeding layer of petals against the petals adjacent on the outside so that, progressing toward the center of the flower, these petals approach a vertical position with increasing degree, until the center petals are often almost or entirely vertical in position. Such flowers are further unique in the degree of color constancy under a variety of weather conditions.

To the best of my knowledge, this new variety of rose contains the least amount of discernible blue pigment of any red rose available to commerce. The general color effect is near Currant Red (Wilson, Plate 821/1, page 167) in newly open flower, and remains this color, although becoming a somewhat intensified hue as the flower ages. Because of the appearance of the inner surface of the petal, there is a slight iridescence, which, viewed at certain angles, gives the effect of variations in color somewhat deeper than the shade above described.

In the drawing are shown specimens of the new variety at different stages of development of the bloom from bud to full-open flower and foliage from young to mature leaves.

Asexual reproduction shows that these characteristics hold true through succeeding propagations.

The following is a detailed description of the new variety, all reference to color being in accordance with the R. F. Wilson's Horticultural Colour Chart, except where indicated to be in accordance with Ridgway's Color Standard and Nomenclature:

Type: Bush; seedling; for cut flowers and garden decoration.
Class: Hybrid tea.
Breeding: Seedling.
*Seed parent.*—"Charlotte Armstrong."
*Pollen parent.*—"Piccaninny."
Propagation: By budding, the only method tried so far.

*Flower*

Locality where grown: Ontario, California.
Flowers borne: Usually singly to stem; on normal, short to medium stems.
Quantity of bloom: Free; outdoors.
Continuity: Continuous during growing season.
Fragrance: Moderate; spicy.
Bud:
*Peduncle.*—Short to medium; medium heavy; medium stiff; medium rough; numerous gland-tipped cilia. Color—Deep Chrysolite Green, Plate XXXI (Ridgway) blotched with near Vandyke Red, Plate XIII (Ridgway) on side exposed to sun.
*Before calyx breaks.*—*Size*—small to medium. *Form*—short; pointed; with foliaceous appendages, gland-tipped cilia, on the surface of the bud; with slender foliaceous parts extending beyond the tip of the bud equal to one-half or more of its length.
*As calyx breaks.*—*Color*—Indian Lake, Plate 826, page 170, with Maroon, Plate 1030/1, page 185, shading. Inner surface—with fine, woolly tomentum. Both margins have stipitate glands and wooly tomentum unless an adjacent sepal covers a margin, and then such covered margin is lined with woolly tomentum only.
*As first petal opens.*—*Size*—medium. *Form*—medium length; ovoid. *Color*—Outside: near Indian Lake, Plate 826/1, page 170, with Maroon, Plate 1030/1, page 185, shadings; inside: Chrysanthemum Crimson, Plate 824, page 169, with Maroon, Plate 1030/1, page 185, shading.
*Opening.*—Opens up well.
Bloom:
*Size.*—When fully open—medium; 3¼ inches to 4 inches.
*Petalage.*—Double; from 28 to 32 petals plus 2 to 3 petaloids, arranged regularly.

*Form.*—High center at first; becoming open with outer petals horizontal but with inside petals approaching a vertical position with increasing degree progressing toward center of flower. This change in petal direction is caused by the reflexing of the lateral margins of the petals in such a way as to cause them to have a slender linear-oblong appearance in outline. Petals remaining at first loosely reflexed at lateral margins; becoming later, at maturity, tightly reflexed at lateral margins.

Petals: Thick; leathery; with inside velvety and outside shiny to satiny.

*Shape.*—Outside—obovate, with apex flat. Intermediate—obovate-cuneate with apex acute. Inside—narrowly obovate-cuneate with apex acute.

*Color.*—Colors may be modified by being shaded with other colors.

This description of a newly opened flower was made from a rose grown outdoors in the month of October, 1945, at Ontario, California:

*Color.*—*Outside petal*—outside surface: near Cardinal Red, Plate 822, page 168; inside surface: near Currant Red, Plate 821/1, page 167, with Indian Lake, Plate 826, page 170, shading. *Intermediate petal*—outside surface: near Cardinal Red, Plate 822/3, page 168; inside surface: near Currant Red, Plate 821/1, page 167, varied somewhat by a slight iridescence. *Inner petal*—outside surface: near Cardinal Red, Plate 822/3, page 168; inside surface: near Currant Red, Plate 821/1, page 167, varied somewhat by a slight iridescence.

This description was made from a rose that was open for three days outdoors in the month of October, 1945, at Ontario, California:

*Color.*—*Outside petal*—outside surface: near Cardinal Red, Plate 822, page 168; inside surface: near Current Red, Plate 821, page 167, with Indian Lake, Plate 826, page 170, shading. *Inside petal*—outside surface: near Cardinal Red, Plate 822/1, page 168; inside surface: near Currant Red, Plate 821/3, page 167, varied somewhat by a slight iridescence.

*General color effect.*—Newly opened flower—near Currant Red, Plate 821/1, page 167, varied somewhat by a slight iridescence. Three days open—near Currant Red, Plate 821/3, page 167, varied somewhat by a slight iridescence.

*Behavior.*—Only a few petals persist. Fades very little.

*Flower longevity.*—On bush in garden—three to four days in October. Cut roses grown outdoors kept at living room temperatures—three to four days in October.

*Reproductive organs*

Stamens: Few to medium number; arranged regularly about pistils, mixed with petaloids.

Filaments: Short to medium; near Fire Red, plate 15/1, page 15; most with anthers.

Anthers: Small to medium; all open at once; near Saffron Yellow, Plate 7/1, page 7, slightly blushed with Carmine Rose, Plate 621/2, page 75.

Pollen: Abundant, near Indian Yellow, Plate 6, page 6.

Pistils: Medium to many, approximately 60 in number.

Styles: Uneven; short to medium; medium heavy; loosely bunched.

*Color.*—Orient Red, Plate 819, page 165, gradually becoming lighter at base.

Stigma: Grayish white bordered by Orient Red, Plate 819, page 165.

Ovaries: All enclosed in calyx.

Hips: Short; globular; near Lime Green, Plate XXXI (Ridgway), mature hips becoming blushed with Etruscan Red, Plate XXVII (Ridgway), having a corky overgrowth near Sayal Brown, Plate XXIX (Ridgway); moderately rough; walls thin to medium fleshy.

Sepals: Permanent; moderately short; recurved.

*Color.*—Inside—Light Grape Green, Plate XLI (Ridgway) at base gradually becoming Deep Grape Green, Plate XLI (Ridgway), washed with Pompeian Red, Plate XIII (Ridgway)—sepals taken from a fully-open flower. Outside—near Rainette Green, Plate XXXI (Ridgway), to near Absinthe Green, Plate XXXI (Ridgway), at base.

Seeds: Few; medium size; 4 to 12 in number.

*Plant*

Foliage:

*Leaves.*—Compound of five to seven leaflets; normally abundant; medium size; leathery.

*Leaflets.*—Shape—oval with apex acute. Base—obtuse. Margin simply serrate.

*Color.*—*Mature*—upper surface: near Cress Green Plate XXXI (Ridgway); under surface: near Asphodel Green, Plate XLI (Ridgway). *Young*—upper surface: near Rainette Green, Plate XXXI (Ridgway), washed with Vandyke Red, Plate XIII (Ridgway); under surface: near Asphodel Green, Plate XLI (Ridgway), washed with Vandyke Red, Plate XIII (Ridgway).

*Rachis.*—Medium heavy. Upper side—grooved; glandular. Under side—moderately prickly and with stipitate glands.

*Stipules.*—Medium long; medium wide; with moderately short points, turning out at an angle of more than 45°.

*Disease.*—Relatively resistant to mildew.

Growth:

*Habit.*—Upright spreading; much branched.

*Growth.*—Moderate.

*Canes.*—Medium heavy.

*Main stems.*—Near Rainette Green, Plate XXXI (Ridgway). *Large prickles*—few to several; medium length; slightly hooked downward; with short somewhat rounded base (somewhat dilated at base). Color—Avellaneous, Plate XL (Ridgway). *Small prickles*—very few. Color—Avellaneous, Plate XL (Ridgway). Slightly dilated at base. *Hairs*—none.

*Branches*—(Semi-hard-wood); near Light Elm Green, Plate XVII (Ridgway). *Large prickles*—Few; short to medium; hooked downward; with short somewhat narrow base. Color—Deep Brownish Vinaceous, Plate XXXIX (Ridgway). *Small prickles*—several; Deep Brownish Vinaceous, Plate XXXIX (Ridgway). *Hairs*—None, but several stipitate glands.

*New shoots.*—Near Biscay Green, Plate XVII (Ridgway) washed with Vandyke Red, Plate XIII (Ridgway), particularly on side exposed to sun. *Large prickles*—Few; short to medium; hooked downward; with somewhat narrow base; near Vandyke Red, Plate XIII (Ridgway). *Small prickles*—several; near Vandyke Red, Plate XIII (Ridgway). *Hairs*—none, but several stipitate glands.

I claim:

A new and distinct variety of rose plant characterized as to novelty by its habit of growth and branching, its vigor, the size, shape, texture, and appearance of the leaves, the shape of the open flower and reflex habit and form of development of the petals thereof, and the red color of said flowers, particularly the near-absence therefrom of discernible blue pigment, substantially as shown and described.

HERBERT C. SWIM.